(12) United States Patent
Soma et al.

(10) Patent No.: US 11,278,564 B2
(45) Date of Patent: Mar. 22, 2022

(54) BRAIN FUNCTION-IMPROVING AGENT, FOOD, AND MEDICINE USING LIPOPOLYSACCHARIDE

(71) Applicants: Control of Innate Immunity Technology Research Association, Takamatsu (JP); National University Corporation Kagawa University, Takamatsu (JP); BioMedical Research Group Inc., Tokyo (JP); Macrophi Inc., Takamatsu (JP)

(72) Inventors: Gen-Ichiro Soma, Tokyo (JP); Hiroyuki Inagawa, Takamatsu (JP); Chie Kohchi, Takamatsu (JP); Yutaro Kobayashi, Kita-gun (JP)

(73) Assignees: Control of Innate Immunity Technology Research Association, Takamatsu (JP); National University Corporation Kagawa University, Takamatsu (JP); BioMedical Research Group Inc., Tokyo (JP); Macrophi Inc., Takamatsu (JP)

( * ) Notice: Subject to any disclaimer, the term of this patent is extended or adjusted under 35 U.S.C. 154(b) by 96 days.

(21) Appl. No.: 16/617,540

(22) PCT Filed: Dec. 4, 2017

(86) PCT No.: PCT/JP2017/043429
§ 371 (c)(1),
(2) Date: Nov. 27, 2019

(87) PCT Pub. No.: WO2018/220886
PCT Pub. Date: Dec. 6, 2018

(65) Prior Publication Data
US 2020/0179436 A1    Jun. 11, 2020

(30) Foreign Application Priority Data

May 28, 2017  (JP) .............................. JP2017-105133

(51) Int. Cl.
*A61K 31/739*     (2006.01)
*A61P 25/28*      (2006.01)
(Continued)

(52) U.S. Cl.
CPC .......... *A61K 31/739* (2013.01); *A23L 33/135* (2016.08); *A61K 35/741* (2013.01); *A61P 25/28* (2018.01); *A61K 9/0053* (2013.01)

(58) Field of Classification Search
None
See application file for complete search history.

(56) References Cited

U.S. PATENT DOCUMENTS

2007/0172492 A1    7/2007    Soma et al.

FOREIGN PATENT DOCUMENTS

| JP | 2011-193877 A | 10/2011 |
| JP | 2016-193865 A | 11/2016 |

OTHER PUBLICATIONS

Reitz, C., "Dyslipidemia and the Risk of Alzheimer's Disease" Curr Atheroscler Rep vol. 15 p. 307 DOI 10.1007/s11883-012-0307-3 (Year: 2013).*

(Continued)

*Primary Examiner* — Eric Olson
(74) *Attorney, Agent, or Firm* — Locke Lord LLP; James E. Armstrong, IV; Nicholas J. DiCeglie, Jr.

(57) ABSTRACT

A readily-available brain function-improving agent or food composition having an Aβ intracerebral deposition suppressing effect or a learning function-improving effect is provided based on finding, as a result of orally administering *Pantoea* LPS to Alzheimer's disease model mice and study- (Continued)

ing the effects, that oral administration of *Pantoea* LPS significantly decreased intracerebral Aβ peptide accumulation and improved learning function.

8 Claims, 4 Drawing Sheets

(51) Int. Cl.
  *A23L 33/135* (2016.01)
  *A61K 35/741* (2015.01)
  *A61K 9/00* (2006.01)

(56) References Cited

OTHER PUBLICATIONS

Jick et al., "Statins and the Risk of Dementia" The Lancet vol. 356 pp. 1627-1631 (Year: 2000).*
Yaffe et al., "Serum Lipoprotein Levels, Statin Use, and Cognitive Function in Older Women" Archives of Neurology vol. 59 pp. 378-384 (Year: 2002).*
Moreira et al., "Effects of lifestyle modifications on cognitive impairments in a mouse model of hypercholesterolemia" Neuroscience Letters vol. 541 pp. 193-198 http://dx.doi.org/10.1016/j.neulet.2013.02.043 (Year: 2013).*
Bath et al., "Intensive versus Guideline Blood Pressure and Lipid Lowering in Patients with Previous Stroke: Main Results from the Pilot 'Prevention of Decline in Cognition after Stroke Trial' (POD-CAST) Randomised Controlled Trial" PLOS One 12(1) pp. 1-21 DOI :10.1371/journal.pone.0164608 (Year: 2017).*
Henderson et al., "Serum lipids and memory in a population based cohort of middle age women" J Neurol Neurosurg Psychiatry vol. 74 pp. 1530-1535 (Year: 2003).*
Iwata et al., "Disease-modifying therapy for Alzheimer's disease: Challenges and hopes" Neurology and Clinical Neuroscience vol. 1 pp. 49-54 (Year: 2013).*
Briggs et al., "Drug treatments in Alzheimer's disease" Clinical Medicine vol. 16 No. 3 pp. 247-253 (Year: 2016).*
J. Hardy et al., "The Amyloid Hypothesis of Alzheimer's Disease: Progress and Problems on the Road to Therapeutics," Science, vol. 297, Jul. 19, 2002, pp. 353-356 and information sheets, (discussed in the spec).
Y. Ano et al., "Preventive Effects of a Fermented Dairy Product against Alzheimer's Disease and Identification of a Novel Oleamide with Enhanced Microglial Phagocytosis and Anti-Inflammatory Activity," PLOS ONE, 10, Mar. 11, 2015, e0118512, pp. 1-16. (discussed in the spec).
D. Westphal et al., "Chemische Erforschung von Lipopolysacchariden gramnegativer Bakterien," Angewandte Chemie, 66, 1954, pp. 407-417. (discussed in the spec).
D. L. Herber et al., "Microglial Activation is Required for A-Beta Clearance After Intracranial Injection of Lipopolysaccharide in APP Transgenic Mice," Journal of Neuroimmune Pharmacology, 2, 2007, pp. 222-231. (discussed in the spec).
J. P. Michaud et al., "Toll-like receptor 4 stimulation with the detoxified ligand monophosphoryl lipid A improves Alzheimer's disease-related pathology," Proceedings of the National Academy of Sciences of the United States of America, vol. 110, No. 5, Jan. 29, 2013, pp. 1941-1946. (discussed in the spec).
C. Kohchi et al., "Applications of Lipopolysaccharide Derived from Pantoea agglomerans (IP-PA1) for Health Care Based on Macrophage Network Theory," Journal of Bioscience and Bioengineering, vol. 102, No. 6, 2006, pp. 485-496. (discussed in the spec).
M. Fukasaka et al., "A Lipopolysaccharide from Pantoea Agglomerans Is a Promising Adjuvant for Sublingual Vaccines to Induce Systemic and Mucosal Immune Responses in Mice via TLR4 Pathway," PLOS ONE, 10, May 15, 2015, e0126849, pp. 1-15. (discussed in the spec).

Y. Kobayashi et al., "Effect of Lipopolysaccharide Derived from Pantoea agglomerans on the Phagocytic Activity of Amyloid Beta by Primary Murine Microglial Cells," Anticancer Research, 36, 2016, pp. 3693-3698. (discussed in the spec and cited in the ISR).
J. E. Morley et al., "The senescence accelerated mouse (SAMP8) as a model for oxidative stress and Alzheimer's disease," Biochimica et Biophysica Acta, 1822, 2012, pp. 650-656. (discussed in the spec).
J. Mehla et al., "Experimental Induction of Type 2 Diabetes in Aging-Accelerated Mice Triggered Alzheimer-Like Pathology and Memory Deficits," Journal of Alzheimer's Disease, 39(1), 2014, pp. 145-162. (discussed in the spec).
K. Nakata et al., "A mixture of Salacia oblonga extract and IP-PA1 reduces fasting plasma glucose (FPG) and low-density lipoprotein (LDL) cholesterol levels," Nutrition Research and Practice, 5(5), 2011, pp. 435-442. (discussed in the spec).
H. Inagawa et al., "Primed Activation of Macrophages by Oral Administration of Lipopolysaccharide Derived from Pantoea agglomerans", in vivo, vol. 30, 2016, pp. 205-211. (cited in the ISR).
S. Ikeda et al. Discussion of Phagocytosis Function Activation of Pantoea agglomerans-derived LPS in Macrophage Dell Line RAW 264.7. 20th Annual Meeting of the Society of Biotherapeutic Approaches, Program/Abstracts, 2016, p. 42. (cited in the ISR).
International Search Report dated Jan. 23, 2018, issued for PCT/JP2017/043429.
T Suzuki et al., "Effects of a Lipopolysaccharide from Pantoea agglomerans on the Cocaine-Induced Place Preference," Life Sciences, vol. 54, No. 6, Jan. 1, 1994, pp. PL75-PL80.
J Kamei et al., "Antinociceptive Effect of Lipopolysaccharide from Pantoea agglomerans on Streptozotocin-lnduced Diabetic Mice," European Journal of Pharmacology, vol. 251, No. 1, Jan. 4, 1994, pp. 95-98.
J Kamei et al., "Suppression of Hyperalgesia in Streptozotocin-lnduced Diabetic Mice by a Lipopolysaccharide from Pantoea agglomerans," Biological & Pharmaceutical Bulletin, vol. 17, No. 5, Jan. 1, 1994, pp. 632-634.
A Yoshida et al., "Improvement of Allergic Dermatitis via Regulation of the Th1/Th2 Immune System Balance by Macrophages Activated with Lipopolysaccharide Derived from Pantoea agglomerans (IP-PA1)," Anticancer Research, vol. 29, No. 11, Dec. 23, 2009, pp. 4867-4870.
K Nakata et al., "Pantoea agglomerans Lipopolysaccharide Maintains Bone Density in Premenopausal Women: a Randomized, Double-Blind, Placebo-Controlled Trial," Food Science & Nutrition, vol. 2, No. 6, Jul. 16, 2014, pp. 638-646.
Extended European search report issued in European Patent Application No. EP 17911728.8 dated Mar. 9, 2021.
Herber D L et al., "Time-dependent reduction in Aβ levels after intracranial LPS administration in APP transgenic mice," Experimental Neurology, Elsevier, Amsterdam, NL, vol. 190, No. 1, Nov. 1, 2004, pp. 245-253.
Dicarlo G et al., "Intrahippocampal LPS injections reduce A[beta] load in APP+PS1 transgenic mice," Neurobiology of Aging, vol. 22, Jan. 1, 2001, pp. 1007-1012.
Malm Tarja M et al., "Bone-marrow-derived cells contribute to the recruitment of microglial cells in response to [beta]- amyloid deposition in APP/PS1 double transgenic Alzheimer mice," Neurobiology of Disease, vol. 18, No. 1, Feb. 2005, pp. 134-142.
Morgan Dave et al., "Dynamic Complexity of the Microglial Activation Response in Transgenic Models of Amyloid Deposition: Implications for Alzheimer Therapeutics," Journal of neuropathology and experimental neurology, vol. 64, No. 9, Sep. 1, 2005, pp. 743-753.
Quinn J et al., "Inflammation and cerebral amyloidosis are disconnected in an animal model of Alzheimer's disease," Journal of Neuroimmunology, vol. 137, No. 1-2, Feb. 27, 2003, pp. 32-41.
European Patent Office Communication issued in EP 17911728.8, dated Jan. 18, 2022.

* cited by examiner

BRAIN FUNCTION-IMPROVING AGENT, FOOD, AND MEDICINE USING LIPOPOLYSACCHARIDE

TECHNICAL FIELD

The present invention relates to a brain function-improving agent, food, and medicine that contain a lipopolysaccharide.

BACKGROUND ART

In recent years in Japan, whereas the total population has been on the decline, the elderly population of 65 years of age and older has been on the rise year after year. According to the Ministry of Health, Labour and Welfare, the elderly population (2015) has exceeded 33 million and it is said that the percentage of the elderly population has reached 26.7%. With regard to dementia, which is an elderly disorder, the number of patients in Japan currently exceeds 4.60 million and is expected to reach 7.00 million and constitute one in every five elderly persons by 2025. Approximately 60% of dementia patients have Alzheimer's disease, approximately 20% have vascular dementia, and the remainder includes patients with various dementia disorders, such as Lewy body dementia. Clinical symptoms of Alzheimer's disease are cognitive function disorders, such as memory disorder, speech disorder, and psychiatric symptoms, behavioral disorders, etc. As a pathological feature of Alzheimer's disease, abnormal structures, such as senile plaques, which are also called amyloid plaques, and neurofibrillary tangles deposit over a wide range of the cerebral cortex and the hippocampus. Amyloid R proteins (hereinafter simply referred to as "A$\beta$") are main components of amyloid plaques and, in particular, an A$\beta$ peptide constituted of 42 residues (hereinafter simply referred to as "A$\beta$1-42") is high in aggregability and known to serve a critical role in amyloid deposition. The latter are constituted of excessively phosphorylated tau proteins. Currently, the amyloid hypothesis is generally accepted as a pathological cascade of Alzheimer's disease. The time sequence is such that excessive accumulation of A$\beta$ causes formation of amyloid plaques and accumulation of tau proteins (neurofibrillary tangles) and subsequently leads to neurodegeneration and neuronal cell death (NPL 1). Although A$\beta$ appears with aging even in the brains of healthy persons, it is considered that A$\beta$ accumulation is promoted by a genetic mutation of an enzyme involved in A$\beta$ production or by decreased activity of an A$\beta$ breakdown system. Although therapeutic agents targeting a neurotransmitter or a receptor thereof (acetylcholinesterase inhibitors and N-methyl-D-aspartic acid receptor antagonists) have been developed as therapeutic agents for Alzheimer's disease, these are not therapeutic agents that treat pathological changes, such as A$\beta$ accumulation, tau protein aggregation, and are therefore not fundamental therapeutic agents capable of arresting the development of Alzheimer's disease.

On the other hand, microglia, which is a macrophage in brain tissue, has been found to serve important roles in the maintenance of homeostasis in the brain, such as repair of damaged tissue, phagocytic removal of waste products in the brain. Microglia expresses A$\beta$ receptors and performs intake and decomposition of A$\beta$ through phagocytic response, and therefore prevention of Alzheimer's disease caused by excessive accumulation of A$\beta$ can be anticipated by activating A$\beta$ phagocytic ability of microglia. In recent years, the search for a compound having an action enabling activation of the A$\beta$ phagocytic ability of microglia has advanced and effects of food constituents, such as oleic acid amides (NPL 2) and peptides (PTL 1) in in vitro experimental systems have been reported.

Incidentally, a lipopolysaccharide is an outer membrane component of cell walls of gram-negative bacteria. The term endotoxin was given in 1892 to a toxic substance derived from *Vibrio cholerae* and the essence of endotoxin was reported to be a lipopolysaccharide in 1954 (NPL 3). However, it has been reported in recent years that intracranial injection of a lipopolysaccharide into Alzheimer's disease model mice induces activation of microglia and suppresses intracerebral deposition of A$\beta$ (NPL 4). Similarly, it has been reported that intraperitoneal injection of MPL (monophosphoryl lipid A) that is a derivative of lipid A, which is a component of a lipopolysaccharide, and approved as an adjuvant (immunostimulant) exhibits an A$\beta$ intracerebral deposition suppressing action and a learning function-improving action (NPL 5). On the other hand, it has been reported that with oral or percutaneous intake of a lipopolysaccharide, a clear toxicity is not evident and an improving effect against disorders, such as hyperlipidemia, allergies, is exhibited (NPL 6). Soma et al. discovered that one such lipopolysaccharide is a lipopolysaccharide derived from a wheat-symbiotic bacteria *Pantoea agglomerans* (hereinafter simply referred to as "*Pantoea* LPS") and reported a fermentation and culture method for obtaining a lipopolysaccharide that is safe even if added to a cosmetic, a food, a functional food, etc. (PTL 2). Fukasaka et al. reported that in an animal experiment, sublingually administered *Pantoea* LPS acts as an adjuvant and increases immunoactivity of a mucous membrane (NPL 7). Further, Kobayashi et al., by examination using primary cultured cells of mouse brain derived microglia, reported that *Pantoea* LPS increases phagocytic ability with respect to A$\beta$1-42 (NPL 8). Incidentally, an orally administered lipopolysaccharide is hardly absorbed from a digestive tract. Whereas starch, for example, is digested because humans have enzymes (amylase and maltase) that digest starch (a macromolecular polysaccharide formed by $\alpha$1-4 bonding of glucose) (Wikipedia, Starch), a polysaccharide of an LPS has a structure constituted of three to five kinds of hexose or pentose (Wikipedia, Lipopolysaccharide) and is not digested because humans do not have a digestive enzyme that can break down the polysaccharide structure of the LPS. Also, with regard to transport into the brain, even if a lipopolysaccharide is absorbed into blood by oral administration, transport into the brain is decreased further in efficiency due to the presence of the blood-brain barrier, etc., and it is thus considered that an orally administered lipopolysaccharide is unlikely to reach inside the brain. Much more, an A$\beta$ intracerebral deposition suppressing effect or a learning function-improving effect by oral administration of a lipopolysaccharide has not been reported thus far and is not mentioned in any literature.

CITATION LIST

Patent Literature

[PTL 1] JP 2016-193865 A
[PTL 2] JP 2011-193877 A

Non Patent Literature

[NPL 1] J. Hardy et al., Science, 297, 353-356, 2002
[NPL 2] Y. Ano et al., PLOS ONE, 10, e0118512, 2015

[NPL 3] O. Westpal et al., Angewandte Chemie, 66, 407-417, 1954
[NPL 4] D. L. Herber et al., Journal of Neurolmmune Pharmacology, 2, 222-231, 2007
[NPL 5] J. P. Michaud et al., Proceedings of the National Academy of Sciences of the United States of America, 110, 1941-1946, 2013
[NPL 6] C. Kohchi et al., Journal of Bioscience and Bioengineering, 102, 485-496, 2006
[NPL 7] M. Fukasaka et al., PLOS ONE, 10, e0126849, 2015
[NPL 8] Y. Kobayashi et al., Anticancer Research, 36, 3693-3698, 2016
[NPL 9] J. E. Morley et al., Biochimica et Biophysica Acta, 1822, 650-656, 2012
[NPL 10] J. Mehla et al., Journal of Alzheimer's Disease, 39, 145-162, 2014
[NPL 11] K. Nakata et al., Nutrition Research and Practice, 5, 435-442, 2011

SUMMARY OF INVENTION

Technical Problem

An intracerebral Aβ deposition suppressing effect or a learning function-improving effect is considered useful for preventing dementia, especially Alzheimer's disease. The present invention has been made in view of such a background and an object thereof is to provide a brain function-improving agent, food, and medicine having an Aβ intracerebral deposition suppressing effect or a learning function-improving effect by a lipopolysaccharide that is made comparatively readily available by the above-mentioned fermentation culture method (PTL 2).

Solution to Problem

The present inventors diligently carried out research in an effort to solve the above problem. *Pantoea* LPS was orally administered to Alzheimer's disease model mice and the effects were studied. Consequently, the inventors found that the intracerebral Aβ peptide accumulation amount is significantly decreased and learning function is improved by oral administration of *Pantoea* LPS and completed the present invention. A brain function-improving agent of the present invention is an agent for Alzheimer's disease that is characterized in containing *Pantoea* LPS as an effective component.

That is, the present invention has the following arrangements.

(1) A brain function-improving agent, food, or medicine having a lipopolysaccharide constituted of *Pantoea* LPS as an effective component for oral administration, percutaneous administration, or buccal administration.

(2) The brain function-improving agent, food, or medicine according to claim 1, where a brain function that is improved is a cognitive function that has deteriorated due to aging or a brain disorder accompanying aging.

(3) The brain function-improving agent, food, or medicine according to claim 1 containing an effective dose of *Pantoea* LPS.

(4) The brain function-improving agent, food, or medicine according to claim 1 being for preventing Alzheimer's disease.

(5) The brain function-improving agent, food, or medicine according to claim 1 containing *Pantoea* LPS at a proportion of 0.1 to 1 mg/kg body weight per daily dose unit.

By the present invention, a composition, such as a medical agent, food having Alzheimer's disease preventing effects, especially an Aβ intracerebral deposition suppressing effect and a learning function-improving effect, due to *Pantoea* LPS can be provided. *Pantoea* LPS has been confirmed for safety of oral or percutaneous administration in forms for foods, cosmetics, animal diets, etc., and can thus be anticipated for preventive effect with low risk of side effects.

BRIEF DESCRIPTION OF DRAWINGS

FIG. 1 shows results of a training test in a water maze test. It is a graph showing that with five continuous days of training, the time required to reach a platform was shortened with all groups. No difference was found among the groups.

DESCRIPTION OF EMBODIMENTS

A brain function-improving agent and food composition of the present invention contain *Pantoea* LPS.

Here, unless specified otherwise, "*Pantoea* LPS" refers to a lipopolysaccharide obtained by culturing a wheat-symbiotic, gram-negative bacteria, *Pantoea agglomerans*, with wheat flour, hot-water extracting the lipopolysaccharide from the bacterial cells, and removing solids in accordance with a procedure described in PTL 2.

The brain function-improving agent and food of the present invention are capable of improving brain dysfunctions, especially cognitive function disorders, due to aging or brain disorders accompanying aging. Alzheimer's disease, etc., can be given as an example of a brain disorder that accompanies cognitive function disorder.

*Pantoea* LPS of the present invention can be applied to humans, mammals besides humans (domestic animals, such as pigs, cattle, sheep, horses, dogs, cats), birds (poultry, such as chickens, turkeys, ducks), etc.

An administration route and a dosage form of a medical composition of the present invention can be designed as appropriate in accordance with purpose, symptoms, subject age, body weight, etc. Examples of the administration route include oral administration, percutaneous administration, buccal administration, subcutaneous injection, intradermal injection, intraperitoneal injection, intramuscular administration, etc. Oral administration, percutaneous administration, or buccal administration is preferable. As examples of forms of dosage form, powder, granule, liquid, capsule, fine granule, pill, syrup, emulsion, etc., can be given. The medical composition is orally administrable and is effective. Such formulations can be made to contain, in addition to *Pantoea* LPS, any one of various additives allowable as a medicine, for example, a stabilizer, filler, emulsifier, extender, excipient, binder, moisturizer, disintegrator, surfactant, suspending agent, coating agent, colorant, fragrance, flavoring agent, sweetener, preservative, and antioxidant.

The food composition of the present invention may use *Pantoea* LPS as it is or use it in accordance with a conventional method for food compositions, such as mixing with another food or food component. Also, with regard to its form, there are no restrictions in particular and an ordinarily used state of food, for example, anyone of solid (powder, granular, etc.), paste, liquid, or suspended form is allowable. The food composition of the present invention can be arranged as a nutraceutical food, food for specified health use, functional food, health food, nutritional supplementary food, drinkable preparation, soft drink, alcoholic beverage, supplement, animal diet, animal diet additive, etc.

In a case of oral ingestion, the brain function-improving agent or food composition is preferably formulated so as to contain *Pantoea* LPS in a range of 0.1 to 1 mg/kg body weight per day for an adult and can be administered in one dose or dividedly administered over several times. A dose of 0.3 to 1 mg/kg body weight is preferable and 0.5 to 1 mg/kg body weight is more preferable. The dose can be adjusted as appropriate in accordance with various factors, such as subject age, body weight, health state, administration method, and combination with other agents (or food components). In a case of intake over a long period of time for a prophylactic purpose, the dose may be less than the above-mentioned ranges.

EXAMPLE

Although the present invention shall now be described in more detail by way of examples, the present invention is not restricted to the following examples.

[Example 1] Method of Oral Administration Test of *Pantoea* LPS to Alzheimer's Disease Model Mice As *Pantoea* LPS, which was prepared and refined in accordance with a fermentation culture method for lipopolysaccharide developed by Soma et al. (PTL 2) (Lipopolysaccharide, *Pantoea agglomerans* <LPS>; Macrophi Inc.) was used. For experiments, 12- to 14-week-old, male SAMP8 mice (senescence accelerated mouse-prone 8/Ta Slc; Japan SLC, Inc.) were used as Alzheimer's disease model mice and after one week of preliminary rearing, the mice were divided into four groups according to body weight. An animal diet (Research Diet) containing 35% fat was fed and water containing 0.3 or 1 mg/kg body weight/day of *Pantoea* LPS was administered by oral administration by ad libitum drinking. To a control group, the animal diet containing 35% fat or an animal diet (Research Diet) containing 4% fat was fed and water was administered by the same method. The mice were reared in a temperature- and humidity-controlled vivarium under environmental conditions of ad libitum fed, ad libitum drinking, and 12-hour light/12-hour dark. After rearing for 17 weeks, a water maze test described below was performed for one week to evaluate learning function. On the day following the end of the water maze test, blood was sampled from the heart. The brain, liver, and epididymal white adipocytes were removed. The present animal experiment has been approved by the Kagawa University Animal Experiment Committee.

In this example, male SAMP8 mice were used as Alzheimer's disease model mice. The present mice are used as senescence-accelerated model mice due to exhibiting Alzheimer's disease-like symptoms, such as increase in intracerebral Aβ deposition amount, deterioration of learning function with aging (NPL 9). Also, it has been reported that intake of a high-fat diet accelerates progress of Alzheimer's disease by inducing type 2 diabetes-like symptoms, for example, increase in fasting blood glucose level, increase in HbA1c value, etc. (NPL 10).

In the present example, the mice were divided into the following four groups.

(1) NC group: The animal diet containing 4% fat (low-fat animal diet) and water were provided for ad libitum intake.

(2) PC group: The animal diet containing 35% fat (high-fat animal diet) and water were provided for ad libitum intake.

(3) *Pantoea* LPS 0.3 mg/kg body weight/day group: The high-fat animal diet and water containing *Pantoea* LPS (0.3 mg/kg body weight/day) were provided for ad libitum intake.

(4) *Pantoea* LPS 1 mg/kg body weight/day group: The high-fat animal diet and water containing *Pantoea* LPS (1 mg/kg body weight/day) were provided for ad libitum intake.

[Water Maze Test]

(1) Apparatus

Water (23±1° C.) was placed in a cylindrical pool (diameter: 100 cm; depth: 40 cm) and a transparent platform (diameter: 10 cm) was installed so as to be sunk 1 cm below the water surface. A commercially available black ink was added to the water in the pool such that a swimming mouse cannot visually recognize the platform. A commercially available digital camera was installed directly above the pool water surface and swimming of each mouse was recorded by video. Swimming paths were analyzed using an image analysis software, AminalTracker, and in accordance with a method described in "Neuroinformatics, 14, 479-481, 2016."

(2) Procedures

On the day before the test, each mouse was made to swim once to acclimate to the pool. As the procedures, each mouse was left for 20 seconds on the platform fixed 1 cm above the water surface and then made to swim freely for 30 seconds. Thereafter, the mouse was guided onto the platform by an experimenter's hand and left there for 20 seconds. Also, in placing a mouse into the pool, the mouse was made to enter the water facing the wall of the pool and the experimenter moved immediately to a position not visible from the mouse. On the first to fifth day, training was performed to make each mouse memorize the position of the platform. The training was performed four times consecutively per day. In the training procedure, each mouse was placed into the pool from an arbitrary position and made to swim for 60 seconds and search for the platform installed 1 cm below the water surface. The time required to reach the platform was recorded and if the platform could not be reached in 60 seconds, the time was recorded as 60 seconds. Also, a mouse that could not reach the platform in time was guided to the platform by the experimenter's hand. After reaching the platform, the mouse was left there for 20 seconds and then taken out from the pool. A probe test was performed on the sixth day. For the probe test, the platform was removed from the pool, each mouse was made to swim for 60 seconds, and times residing in respective quadrants of the pool were measured. The probe test was performed once for each mouse.

Blood glucose level of blood was measured using a blood glucose level measuring device (Roche Diagnostics) and HbA1c was measured using an enzymatic method measuring kit (Sekisui Medical). Triglycerides, total cholesterol, LDL cholesterol, and HDL cholesterol in serum were measured using an enzymatic method measuring kit (Wako Pure Chemical Industries). Oxidized LDL in serum was measured using an ELISA kit (Kamiya Biomedical Company). Intracerebral Aβ peptide accumulation amount was measured using an ELISA kit (Wako Pure Chemical Industries). In accordance with a protocol in an instruction manual, an Aβ fraction was prepared from each removed mouse cerebrum sample and Aβ1-42 and an Aβ peptide constituted of 40 residues (Aβ1-40) were respectively quantified. The results are expressed by a mean value and a standard error of the mean value (SEM). Also, one-way analysis of variance was performed in accordance with Tukey-Kramer multiple comparisons test. Different symbols indicate that there is a significant difference with P<0.05.

[Results]

With regard to body weight after 18 weeks of rearing, although the PC group had a significant difference in comparison to the NC group, the PC group had no significant difference in comparison to the *Pantoea* LPS administration groups. The fasting blood glucose level is clearly increased in the PC group in comparison to the NC group and is significantly decreased in the *Pantoea* LPS administration groups in comparison to the PC group. Similarly, HbA1c is clearly increased in the PC group in comparison to the NC group and is significantly decreased in the *Pantoea* LPS 1 mg/kg body weight/day group in comparison to the PC group. Also, liver weight and epididymal white fat weight were clearly increased in the PC group in comparison to the NC group and were found to be significantly decreased in the *Pantoea* LPS administration groups in comparison to the PC group (Table 1). From these results, it can be understood that with the mice that ingested the high-fat animal diet, type 2 diabetes-like symptoms (increases in blood glucose level, HbA1c value, etc.) have developed and glucose metabolism function is improved by administration of *Pantoea* LPS.

As a result of analyzing blood lipids, clear decreases in total cholesterol and LDL cholesterol were found in the *Pantoea* LPS administration groups. HDL cholesterol was found to be clearly increased in the *Pantoea* LPS 1 mg/kg body weight/day group in comparison to the PC group. Also, with regard to oxidized LDL, the *Pantoea* LPS 1.0 mg/kg body weight/day group exhibited values much lower in comparison to the PC group than did the *Pantoea* LPS 0.3 mg/kg body weight/day group (Table 1). From these results, it can be understood that in SAMP8 mice that ingested the high-fat animal diet, oral administration of *Pantoea* LPS improves glucose metabolism and lipid metabolism. Thus far, Nakata et al. reported that in an oral administration test of a tea beverage combined with *Pantoea* LPS (0.02% w/w) performed on diabetes model mice (KK-Ay), the fasting blood glucose level significantly decreased in comparison to a control group provided with water, and further reported that in a clinical trial (double-blind randomized comparative trial) of the same tea beverage combined with *Pantoea* LPS, LDL cholesterol decreased and HDL cholesterol increased due to intake of the beverage (NPL 10).

TABLE 1

|  | NC | PC | Pantoea LPS 0.3 mg/kg body weight/day | Pantoea LPS 1 mg/kg body weight/day |
|---|---|---|---|---|
| Initial body weight (g) | 30.4 ± 1.6 [a] | 30.0 ± 0.9 [a] | 28.1 ± 1.2 [a] | 28.5 ± 1.5 [a] |
| Final body weight (g) | 37.7 ± 1.5 [a] | 44.7 ± 0.8 [b] | 41.9 ± 1.5 [a,b] | 43.6 ± 1.8 [a,b] |
| Food intake (g/day) | 3.6 ± 0.1 [a] | 4.0 ± 0.2 [a] | 4.1 ± 0.2 [a] | 3.9 ± 0.2 [a] |
| Fasting Blood Glucose (mg/dL) | 119.0 ± 6.6 [a] | 220.5 ± 6.5 [b] | 189.9 ± 6.6 [c] | 193.9 ± 5.4 [c] |
| HbA1c (%) | 3.4 ± 0.1 [a] | 4.4 ± 0.2 [b] | 4.0 ± 0.1 [a,b] | 3.8 ± 0.1 [a] |
| Liver (g) | 1.7 ± 0.1 [a] | 2.4 ± 0.1 [b] | 1.8 ± 0.1 [a] | 1.9 ± 0.1 [a] |
| Epididymal fat (g) | 1.0 ± 0.1 [a] | 1.3 ± 0.1 [b] | 1.0 ± 0.1 [a] | 1.1 ± 0.1 [a] |
| Plasma lipid (mg/dL) |  |  |  |  |
| Total cholesterol | 49.5 ± 9.3 [a] | 143.8 ± 5.2 [b] | 88.6 ± 9.9 [c] | 68.1 ± 7.5 [a,c] |
| LDL cholesterol | 3.9 ± 1.3 [a] | 16.8 ± 4.6 [b] | 8.0 ± 2.0 [a,b] | 5.2 ± 0.7 [a] |
| HDL cholesterol | 44.3 ± 5.5 [a,b] | 39.0 ± 4.3 [b,c] | 39.0 ± 2.7 [b,c] | 54.0 ± 3.8 [a] |
| Plasma oxidized LDL (ng/mL) | 186.7 ± 16.7 [a] | 407.2 ± 38.1 [b] | 342.7 ± 47.6 [b,c] | 256.7 ± 1.41 [a,c] |

Figure 1:
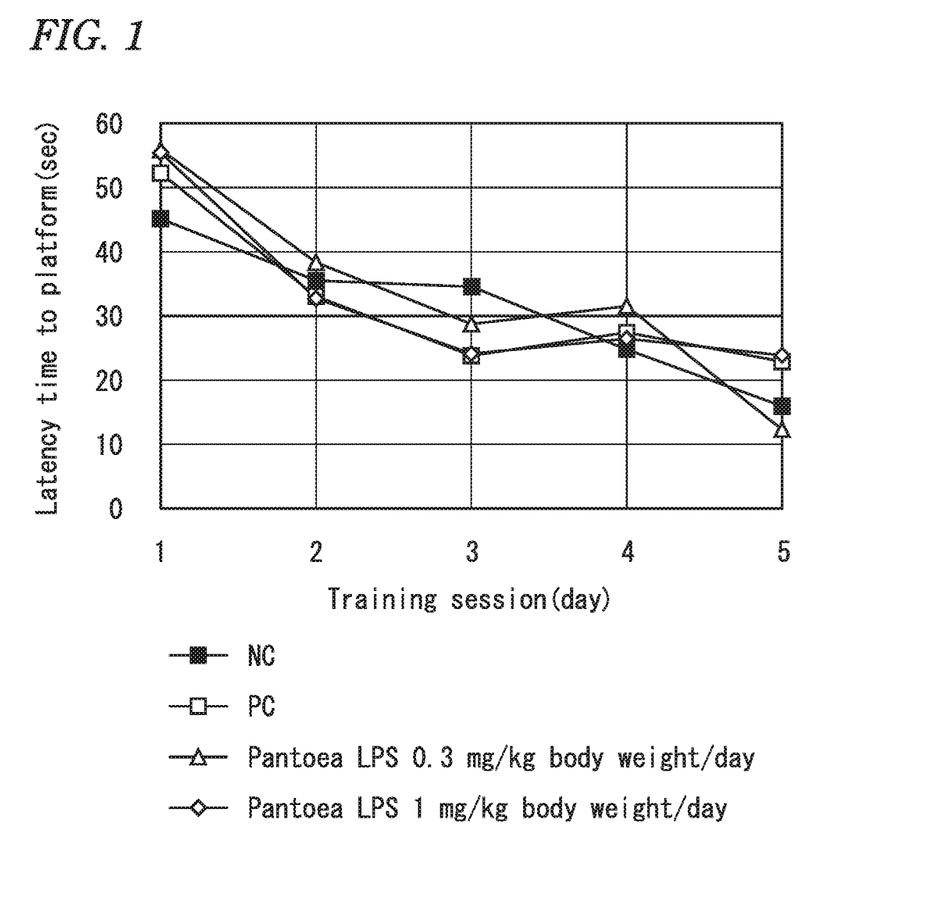
Figure 2:
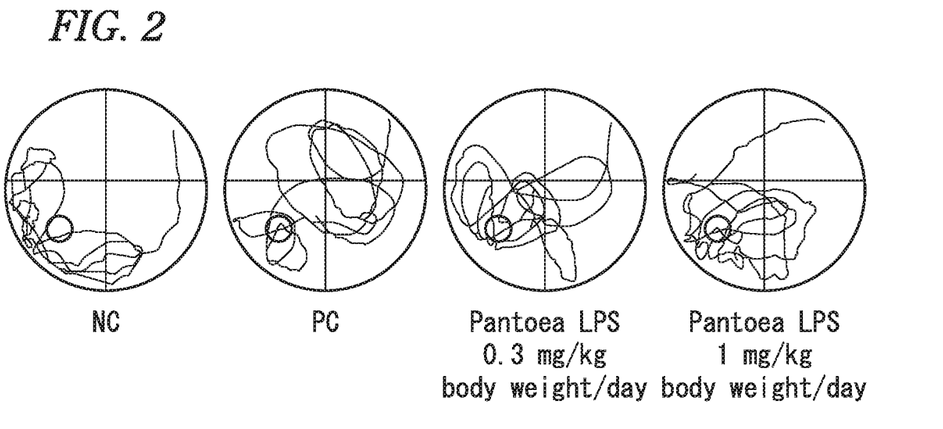
FIG. 2 shows representative swimming paths in a probe test of the water maze test. The dotted line circle indicates the position at which a platform was installed.
Figure 3:
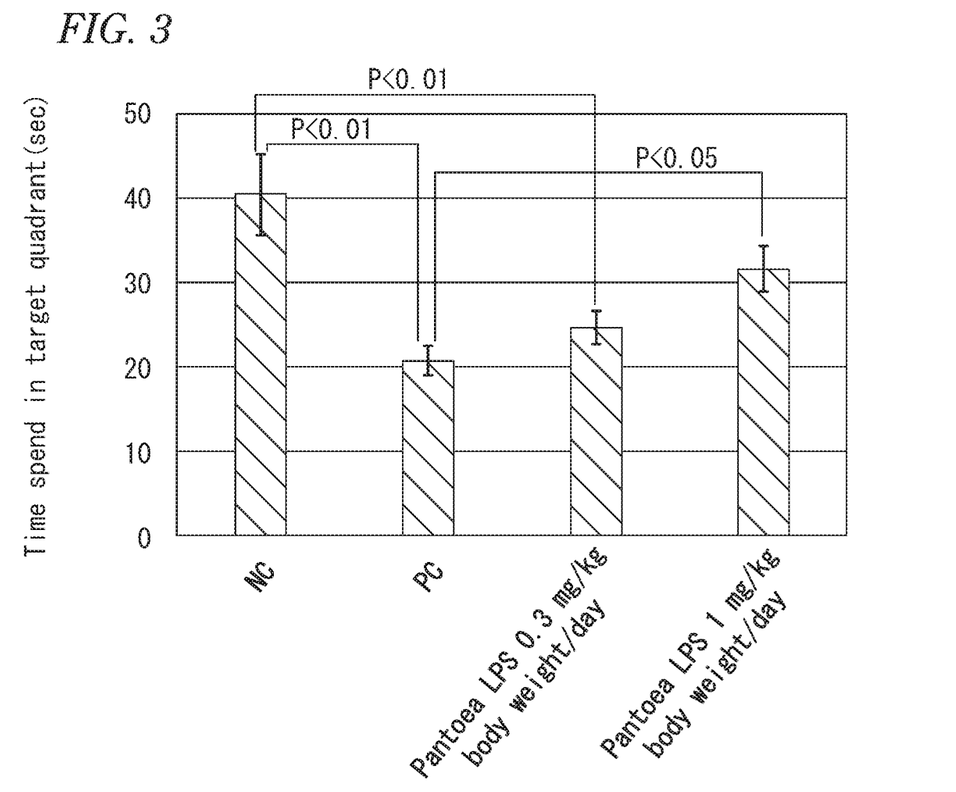
FIG. 3 shows results of times during which mice resided in a quadrant in which the platform was installed in the probe test of the water maze test. The results show that although a decrease in the residence time was found with a PC group that ingested a high-fat diet, *Pantoea* LPS intake extends the residence time.

Although as a result of performing the training test of the water maze test, it was found that in all groups, the time required to reach the platform was reduced through five days of training, differences among the groups were not found (FIG. 1). The probe test was performed on the day following the training test. Representative data of the swimming tracks of the mice are shown for the respective groups in FIG. 2. With regard to time residing in the quadrant in which the platform was installed, a clear decrease was found in the PC group in comparison to the NC group. Also, the time was comparatively longer in the *Pantoea* LPS 1.0 mg/kg body weight/day than in the *Pantoea* LPS 0.3 mg/kg body weight/day in comparison to the PC group (FIG. 3). From the results of the learning function evaluation based on the water maze test, it can be understood that a brain function related to learning function of Alzheimer's disease developing (senescence-accelerated) model mice is improved by oral administration of *Pantoea* LPS.

Figure 4A:
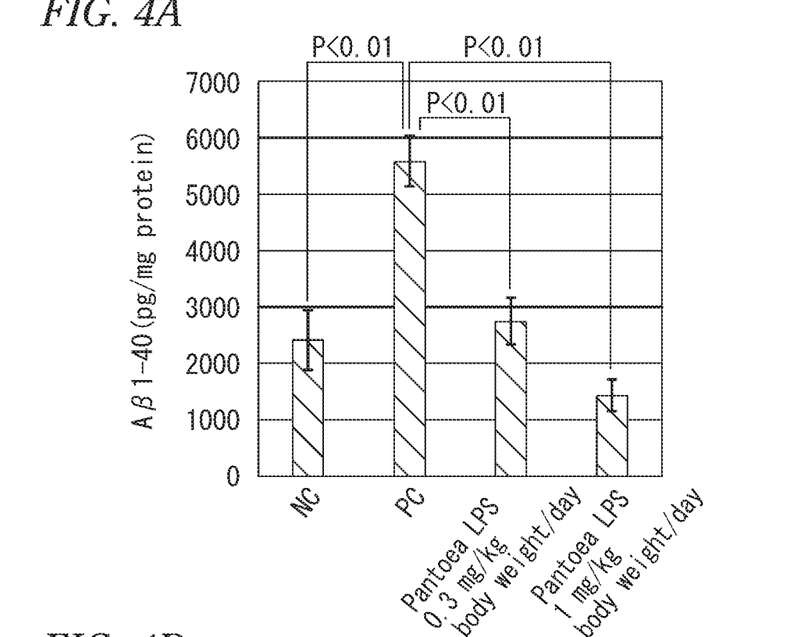
FIGS. 4A and 4B show accumulation amounts of Aβ (Aβ1-40 and Aβ1-42) in brains removed from mice after 18 weeks of rearing. The results show that in comparison to an NC group, a significant increase in Aβ1-40 amount was found in the PC group that ingested the high-fat diet and that *Pantoea* LPS intake decreases the Aβ1-40 and Aβ1-42 amounts significantly in comparison to the PC group.
Figure 4B:
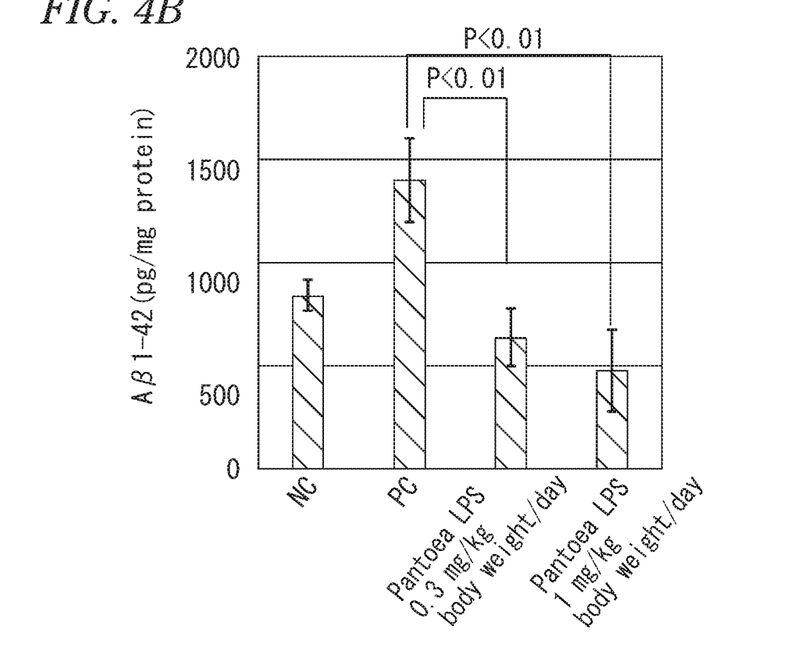

As a result of measuring the intracerebral Aβ accumulation amount by ELISA, it was found that Aβ1-40 was clearly increased in the PC group in comparison to the NC group and was significantly decreased in the *Pantoea* LPS administration groups in comparison to the PC group. Also, with regard to Aβ1-42, although a significant difference was not found between the NC group and the PC group, significant decreases were found in the *Pantoea* LPS administration groups in comparison to the PC group (FIGS. 4A and 4B). From these results, it can be understood that *Pantoea* LPS suppresses intracerebral accumulation of Aβ to suppress onset of Alzheimer's disease (functional deterioration of learning function, etc.).

All publications, patents, and patent applications cited in the present description are incorporated in entirety as reference herein.

Also, the disclosure, including the description, claims, and drawings, of Japanese Patent Application No. 2017-105133 applied on May 28, 2017 is herein incorporated in entirety as reference.

The invention claimed is:

1. A method for improving a brain function in a human or animal in need thereof comprising administering a dose of a lipopolysaccharide constituted of *Pantoea* LPS as an effective component by oral administration, percutaneous administration, or buccal administration in the form of an agent, food, or medicine.

2. The method for improving the brain function according to claim 1, wherein the brain function that is improved is a cognitive function that has deteriorated due to aging or a brain disorder accompanying aging.

3. The method for improving the brain function according to claim 1 wherein the does is an effective dose of *Pantoea* LPS.

4. The method for improving the brain function according to claim 1 being for preventing Alzheimer's disease.

5. The method for improving the brain function according to claim 1 containing *Pantoea* LPS at a proportion of 0.1 to 1 mg/kg body weight per daily dose unit.

6. The method for improving the brain function according to claim 1 containing *Pantoea* LPS at a proportion of 0.3 to 1 mg/kg body weight per daily dose unit.

7. The method for improving the brain function according to claim 1 containing *Pantoea* LPS at a proportion of 0.5 to 1 mg/kg body weight per daily dose unit.

8. The method for improving the brain function according to claim 1 containing an effective dose of *Pantoea* LPS, 0.02% w/w, by an oral administration of a tea beverage.

* * * * *